US007806488B2

(12) United States Patent
Hannan et al.

(10) Patent No.: US 7,806,488 B2
(45) Date of Patent: Oct. 5, 2010

(54) MEDICATION CART DRAWER LINER AND METHOD FOR USING SAME TO REDUCE NOSOCOMIAL INFECTIONS

(75) Inventors: Robin E Hannan, Romeoville, IL (US); Curtis A. Hannan, Romeoville, IL (US)

(73) Assignee: DBL Solution, Inc, Romeoville, IL (US)

( * ) Notice: Subject to any disclaimer, the term of this patent is extended or adjusted under 35 U.S.C. 154(b) by 0 days.

(21) Appl. No.: 12/478,974

(22) Filed: Jun. 5, 2009

(65) Prior Publication Data

US 2009/0242453 A1 Oct. 1, 2009

Related U.S. Application Data

(63) Continuation of application No. 10/795,823, filed on Mar. 8, 2004, and a continuation of application No. 10/246,058, filed on Sep. 18, 2002.

(51) Int. Cl.
*A61B 19/02* (2006.01)

(52) U.S. Cl. ................ 312/209; 312/249.11; 312/348.3

(58) Field of Classification Search .............. 312/348.3, 312/291, 249.11, 209; 220/561, 459.5, 505–507; 206/8, 23.83, 405, 408, 410
See application file for complete search history.

(56) References Cited

U.S. PATENT DOCUMENTS 1,674,222 A * 6/1928 Quigley ....................... 40/359
2,919,200 A 12/1959 Dubin et al.
3,241,898 A 3/1966 Propst
3,834,778 A 9/1974 Morrison et al.
4,019,793 A 4/1977 Gerding
5,377,839 A 1/1995 Relyea et al.
5,673,983 A 10/1997 Carlson et al.
5,883,806 A 3/1999 Meador et al.
6,039,467 A 3/2000 Holmes
6,305,567 B1 10/2001 Sulpizio
6,378,963 B1 4/2002 Relyea et al.
6,386,386 B1 * 5/2002 George ....................... 220/526
6,640,159 B2 10/2003 Holmes et al.

FOREIGN PATENT DOCUMENTS

DE 3810531 A1 10/1989
JP 05228032 A 9/1993

* cited by examiner

*Primary Examiner*—Hanh V Tran
(74) *Attorney, Agent, or Firm*—Michael P Mazza, LLC

(57) ABSTRACT

In a medication storage cart or ADM machine housing a plurality of individual drawers or bins holding medication and/or medical equipment, the invention provides devices and a method for reducing the risk of nosocomial infection through the use of disposable liners. Disposable liners may be placed within the bins, within drawer liners, or within cubies or mini-drawers. In some applications the liners may be color-coded for a predetermined use or patient compartmentalized with dividers, or customized with special labels. The disposable liners may have a tapered form so that multiple liners may be stored in a nested stack to minimize space requirements and to be loaded into a liner dispenser system.

12 Claims, 12 Drawing Sheets

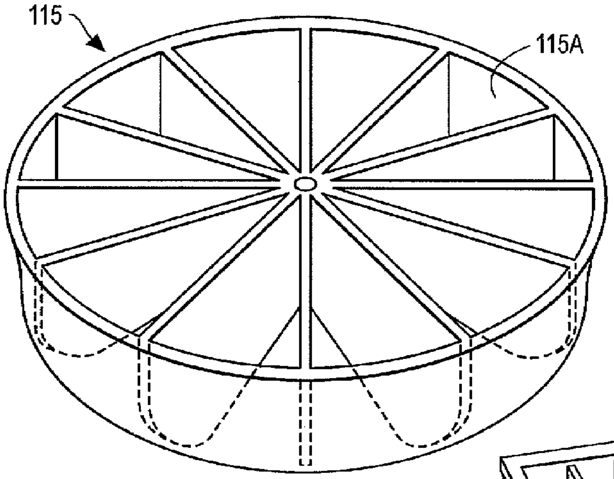
Fig. 14
Prior Art
Fig. 15B
Prior Art
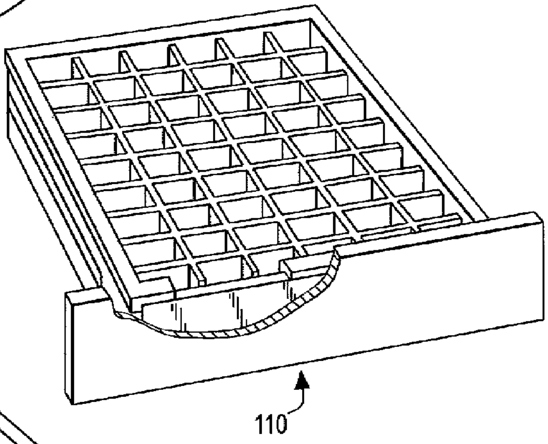
Fig. 15A
Prior Art
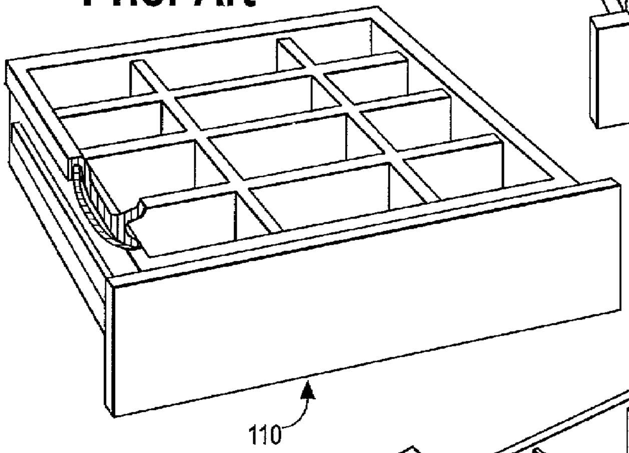
Fig. 15C
Prior Art
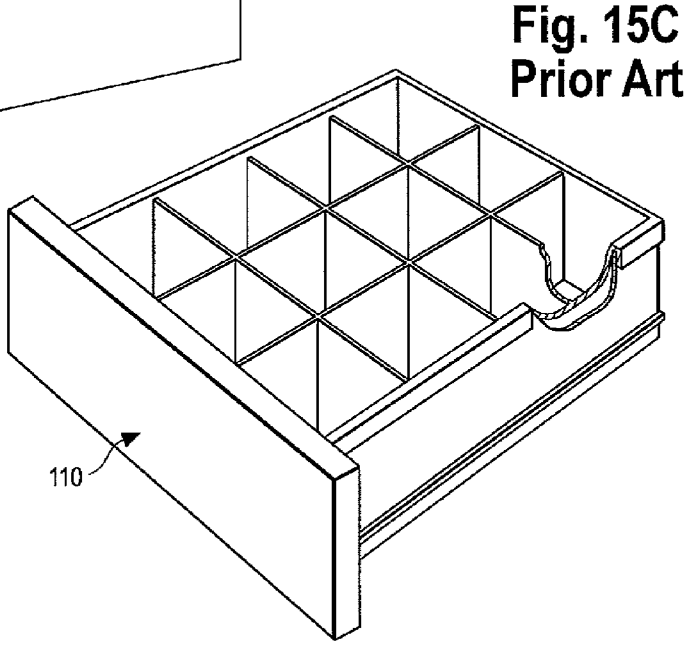

MEDICATION CART DRAWER LINER AND METHOD FOR USING SAME TO REDUCE NOSOCOMIAL INFECTIONS

PRIORITY CLAIM

This application is a continuation-in-part of U.S. application Ser. No. 10/795,823 filed Mar. 8, 2004, which is a continuation-in-part of U.S. application Ser. No. 10/246,058 filed Sep. 18, 2002.

FIELD OF THE INVENTION

The present invention relates generally to patient care equipment used in hospitals, nursing homes, psychiatric centers, hospitals and similar facilities. More particularly, the invention relates to methods and apparatus for storing and dispensing medicines and other patient care supplies in a manner that reduces the risk of infection and cross-contamination.

BACKGROUND OF THE INVENTION

It is a known problem that patients entering a hospital or other care giving facility are at risk of contracting infections and other diseases that are the result not of the patients' underlying illness, but of the patients' close proximity to and contact with patient care equipment and personnel during treatment. These inflictions, known as nosocomial infections, may have a variety of sources. For example, even though patient care equipment or medicine may be sterile, if the container holding the equipment is not also sterile an infectious agent may be transmitted from the container to the equipment and ultimately to the patient. The Center for Disease Control estimates that 1 in 20 patients (2 million per year) acquire infections in the hospital. It is estimated that nosocomial infections from all microorganisms directly cause 19,000 deaths per year and contribute to 58,000 deaths per year, which makes them the $11^{th}$ leading cause of death in the US.

Normally, hospitals and other patient care facilities classify nosocomial infection prevention measures into three general categories, based on the nature of the patient care equipment involved. Critical items (such as surgical instruments, catheters and implants) are sterilized, with the objective of destroying all forms of microbial life. Semicritical items (such as fiberoptic endoscopes and endotracheal tubes) often are subjected to a disinfection procedure. Disinfection in this context is intended to destroy vegetative microorganisms, most fungal spores, tubercle bacilii, and small nonlipid viruses. Noncritical items (such as medication carts, bins, bedboards and blood pressure cuffs) receive a simple cleaning which is designed to remove rather than to kill microorganisms.

An underestimated problem with traditional three-tiered prevention measures is the cross-contact between critical, semicritical and noncritical patient care items in the course of treatment. An additional complicating factor is the interaction of patient care personnel with these items in the course of providing treatment to patients. Specifically, the present invention is directed to reducing the risk of nosocomial infection transmission through cross-contact related to the use and care of medication carts.

Commonly, medication carts are comprised of multiple metal or plastic drawers or bins (used as interchangeable terms in this specification) in a mobile cabinet. The drawers are filled with medication in various solid or liquid forms and related patient care equipment. Each medication drawer is designated for the use of a single patient. Ideally, when a patient is released or transferred, or after a predetermined passage of time, that drawer is cleaned and reused for another patient. Presently, however, there are no standards or documented procedures for the cleaning and reusing of medication bins. Bins are frequently reused without the necessary cleaning, in part because a lack of adequate cleaning does not hinder the use of the bin as a container for medication or patient care equipment. In addition, bins are commonly designated to a specific patient by gummed labels that are only partially removable after use. Subsequent labels sometimes fall off and the sticky residue from multiple labels becomes another potential host site for bacteria and pathogens which may be transferred to the medication and then to the patient through repeated contact by the caregiver with the host site in the process of providing curative or palliative care.

It is therefore a problem with conventional medication bins that the bins receive inadequate cleaning and become a site for the transmission of nosocomial infections. What is needed is a way for patient care facilities (or others responsible for the care and maintenance of medication carts) to insure that medication and other patient care equipment is transported to the patient in a medication bin that reliably and repeatedly minimizes the risk of nosocomial infection.

DEFINITION OF CLAIM TERMS

The following terms are used in the claims of the patent as filed and are intended to have their broadest meaning consistent with the requirements of law. Where alternative meanings are possible, the broadest meaning is intended. All words used in the claims are intended to be used in the normal, customary usage of grammar and the English language.

"Liner" means any rigid or semi-rigid material, such as plastic, which is inserted within a bin or drawer, or within an individual compartment (whether formed by another drawer liner, or formed by a "cubie" or "mini-drawer," non-limiting examples of which are shown in FIGS. 13A-13C, 16, 19 and 20) for use in a medication cart, automatic dispensing machine, or other storage device. In one preferred example of the invention, drawer liners integrally include separate compartments, and disposable compartment or "pocket" liners are removably inserted into these compartments (a "liner within a liner").

SUMMARY OF THE INVENTION

The present invention is directed to medication bin liners that are lightweight and disposable after a single use. The invention is also directed to the use of these bin liners. A significant advantage of the present invention over prior art methods and devices is that there is no cleaning step involved. Whenever a bin liner is soiled, it can be immediately disposed of or discarded and replaced with another liner. In one embodiment, the bin liner can have a bottom of sufficient strength so that the medication bin itself does not require a bottom. This embodiment makes it impossible for patient care personnel to use the bins without including a disposable liner.

It is also a feature and an advantage of the present invention, in an alternative embodiment, that each liner has a tapered form that allows multiple liners to be stored in a nested arrangement, saving storage space. The liners may also be color-coded for various applications or patient types and gummed color labels may also be used without need for later removal and replacement. In addition, each liner may be formed to receive dividers for segmenting individual liners into smaller storage spaces. The invention embraces both permanent and disposable dispensing systems to manage the distribution of bin liners at a facility.

Further features of the present invention relate to the use of a sealed cover for the bin liner to protect the contents of the liner during storage and/or transport. In addition, the bin liner may be provided with a variety of bottom configurations to protect the liner contents from inadvertent breakage and/or to facilitate the organized storage or arrangement of the liner contents.

The inventions may be used in patient care and home health care facilities, and at service provider sites for the health care and pharmaceutical industries. Invention applications include uses involving: institutional drug delivery systems (e.g., at hospitals, nursing homes and pharmacies), and other similar drug delivery systems, epidural trays, stock bins for general unit dose dispensing, receptacles for sorting of outpatient medicine, separation of narcotics for individual floors for patient medications/IV pick-up, team-R carts, code carts, cassettes for labor and delivery tackle boxes, cardiovascular operating room buckets, drawer liners for wooden and other types of cabinets or wire storage racks, buckets sent via dumbwaiter, pneumatic tubes for lab and blood-born pathogens (i.e., lab samples), and intravenous room separation of refrigerated IV solutions.

In a preferred embodiment, liners for use in combination with a drawer of a medication storage apparatus are provided, including a first liner sized to fit within the drawer. The first liner may have a plurality of compartments shaped and sized to hold medications. A plurality of second liners are also provided, and sized and adapted to be removably inserted within the plurality of compartments of the first liner. The second liners are preferably designed to be disposable.

The medication storage apparatus may be a manual device such as that shown in FIG. 1, or an automatic dispensing machine (ADM) such as a Pyxis or Omnicell machine and/or as shown in FIG. 11. It may be preferred to make the first liners out of a rigid, clear or opaque plastic material, while it may be preferred to make the second liners from a clear or opaque plastic material. Both types of liners are preferably made of a bacteriostatic plastic.

It may be preferred to adopt a color-coding scheme for the first and/or the second liners. Such a color-coding scheme may be used, for example, to indicate the presence of medications having one or more of the following attributes: addicting; a similar-sounding name; look-alikes; innocuous or common in attributes or use; low therapeutic window; or pronounced therapeutic effects. Of course, it may be desirable to color-code for other medication or equipment attributes, as well.

Depending upon the type of medication storage device used, the liners may also include individual patient-specific information.

As typical with ADM use, upon entry of predesignated information by medical personnel, both the drawer of the ADM and a designated integral compartment automatically open to reveal the contents of the designated compartment. When used with ADMs, the invention may be adopted for use with "matrix" drawers as well as drawers containing "cubies" or "minis" (e.g., in the claims referenced as "a plurality of integral compartments sized and shaped to hold medications of different sizes and shapes, each integral compartment designed to electronically interconnect with the drawer"). Disposable compartment liners may be sized for removable insertion within the "cubies" or "minis."

A method for reducing nosocomial infection in a hospital or other medical patient care facility also forms a part of the invention. In one embodiment of the method of the invention, a medication storage device is provided having one or more drawers for the storage and transporting of medications and/or medical treatment equipment. The medication storage device may be a medication cart with drawers or bins that are manually opened and closed, or an ADM. A first liner is positioned in the one or more drawers of the storage device. The first liner has a plurality of individual compartments for holding the medications and/or medical treatment equipment. A plurality of second liners may then be positioned within the plurality of individual compartments of the first liner. Each of the second liners are preferably sized and shaped for removable insertion within the individual compartments. Medications and/or medical treatment equipment may now be placed within the plurality of individual compartments of the drawer of the storage device having the second liners located therein. Selected medications and/or equipment may be transported to individual patients. The second liners may be periodically removed from the individual compartments of the first liner, and disposed of, and new second liners may be positioned in their place within the individual compartments. The first liners may be periodically cleaned, as well.

Other embodiments in keeping with the principles of the invention will be apparent to those of ordinary skill in the art, particularly after review of the following detailed description of the preferred embodiments and accompanying drawings.

BRIEF DESCRIPTION OF THE DRAWINGS

The novel features which are characteristic of the invention are set forth in the appended claims. The invention itself, however, together with further objects and attendant advantages thereof, will be best understood by reference to the following description taken in connection with the accompanying drawings, in which:

FIGS. 14 and 15A-15C are perspective view of a prior art drawer liner (FIG. 14), or various drawers (FIGS. 15A-15C) with inserted plastic drawer liners, useable with the dispensing machine shown in FIG. 11, and having different drawer liner bin configurations (e.g., pie-shaped, square, rectangular);

Figure 1:
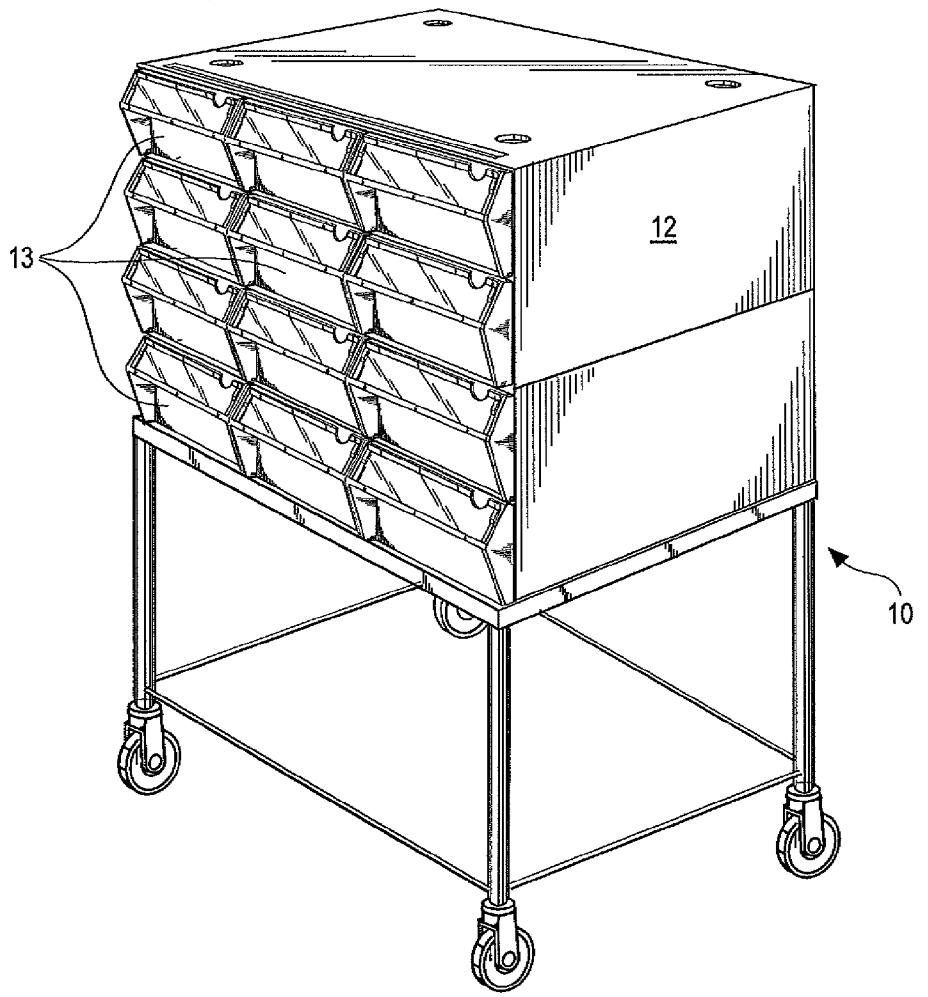
Fig. 1 PRIOR ART
FIG. 1 is a perspective view of an embodiment of a prior art medication cart.

The components in the drawings are not necessarily to scale, emphasis instead being placed upon clearly illustrating the principles of the present invention.

DETAILED DESCRIPTION OF THE PREFERRED EMBODIMENT

Set forth below is a description of what is currently believed to be the preferred embodiment or best example of the invention claimed. Future and present alternatives and modifications to this preferred embodiment are contemplated. Any alternatives or modifications which make insubstantial changes in function, in purpose, in structure or in results are intended to be covered by the appended claims.

FIG. 1 depicts a medication cart 10 that is known in the art and commonly used in patient care facilities. The cart housing 12 is typically constructed of aluminum, steel, or some combination of these materials. In some cases, the cart 10 may also include some molded industrial plastic parts. The interior of the housing 12 may be partitioned to support a plurality of drawers or bins 13 that can be slid or rolled out for access. Typically, medication carts 10 have a single-sided design (as shown in FIG. 1) and may include other accessories such as lock systems, waste containers, countertops (not shown) and other similar features as are known in the art.

Figure 2:
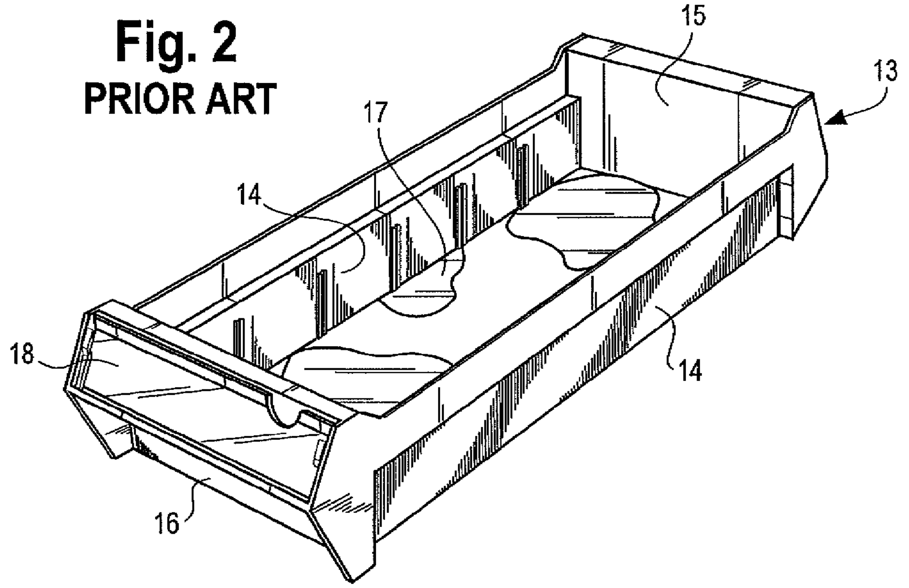
Fig. 2 PRIOR ART
FIG. 2 is a perspective view of a drawer of the medication cart shown in FIG. 1.

Medication cart drawers 13 (FIG. 2) are commonly made of plastic and housed in a metal medication cart 10. Each drawer 13 typically has two side panels 14, an end panel 15, a front panel 16 and a bottom 17. In some variations, the drawer 13 may also have a top (not shown). The front panel 16 of a typical drawer 13 may include an identification plate 18 which is used to hold information about a specific patient. As drawers 13 are used, their interiors 17 become soiled by various spills and by contact with care providers and used patient care equipment.

Figure 3:
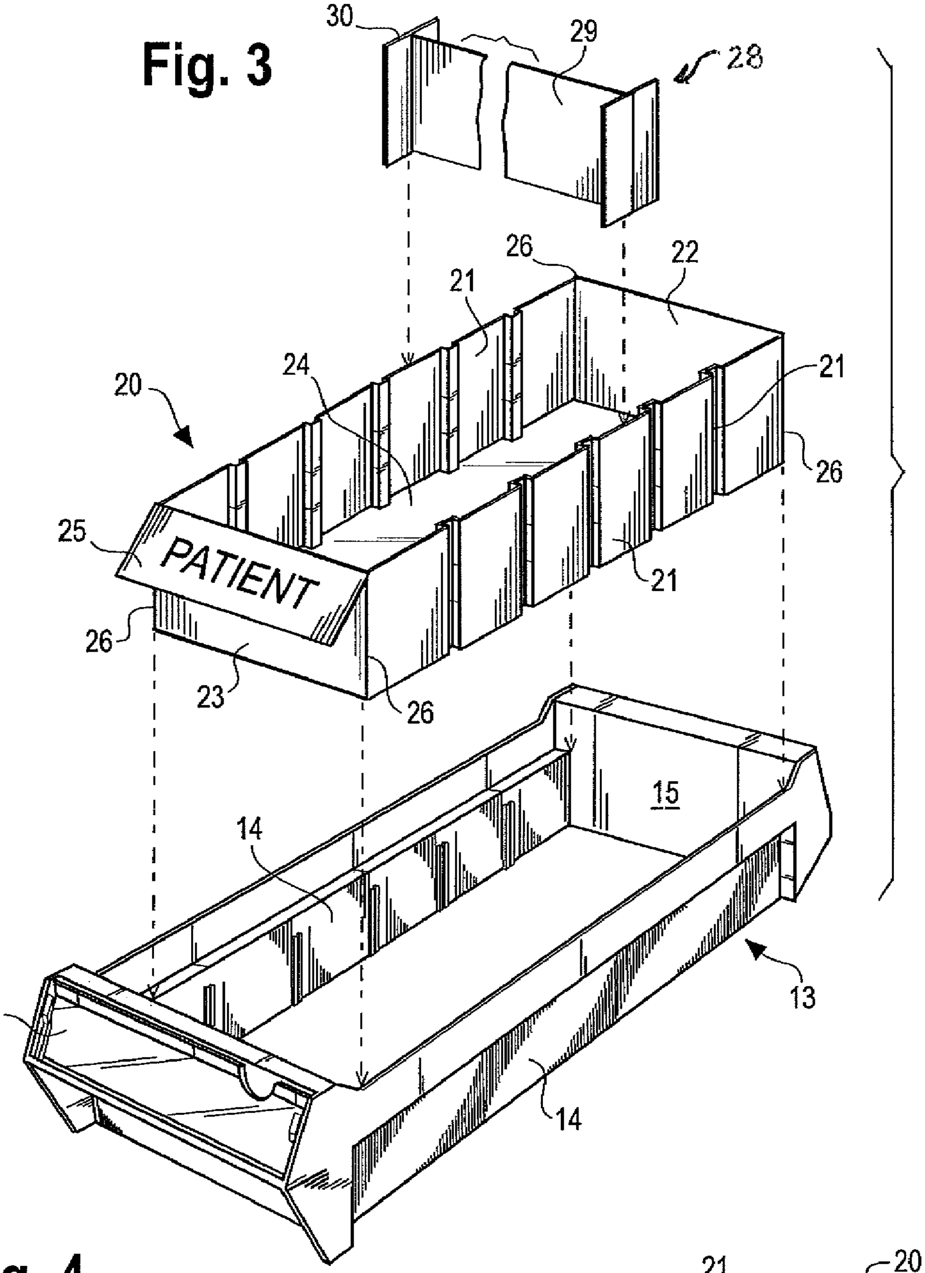
FIG. 3 is a perspective view of the components of one embodiment of the drawer of a medication cart shown in FIG. 2.

In a preferred embodiment of the invention, the drawer 13 is constructed without a bottom. Prior to each use, the drawer 13 receives a liner 20 (see FIG. 3) comprised of two side panels 21, an end panel 22, a front panel 23 and a bottom 24. The liner 20 also may include an identification panel or tab 25 attached to the front panel 23. At the junction of the side panels 21 to the front 23 and end panel 22, the liner corners 26 are tapered so that the bottom panel 24 is smaller than the opening at the top of the liner 20. The side panels 21 of the liner 20 may include inwardly extending channels or ribs 27 spaced so that ribs 27 on opposing side panels 21 are aligned. The ribs 27 may also be positioned to align with vertical rails that may be present on the insides of side panels 14 of drawers 13. Individual ribs 27 may be a constant width (as in FIG. 3) or may be tapered with a narrower width at the top of the liner and a greater width at the bottom (as in FIG. 5). Dividers 28 may be comprised of a center panel 29 and two end tabs 30. In a complete assembly of the preferred embodiment, dividers 28 may be inserted into the liner 20, and the liner 20 may then be positioned within the drawer 13. At the end of a use (an interval defined by the care provider), the liner 20 and dividers 28 may be removed and replaced.

Figure 4:
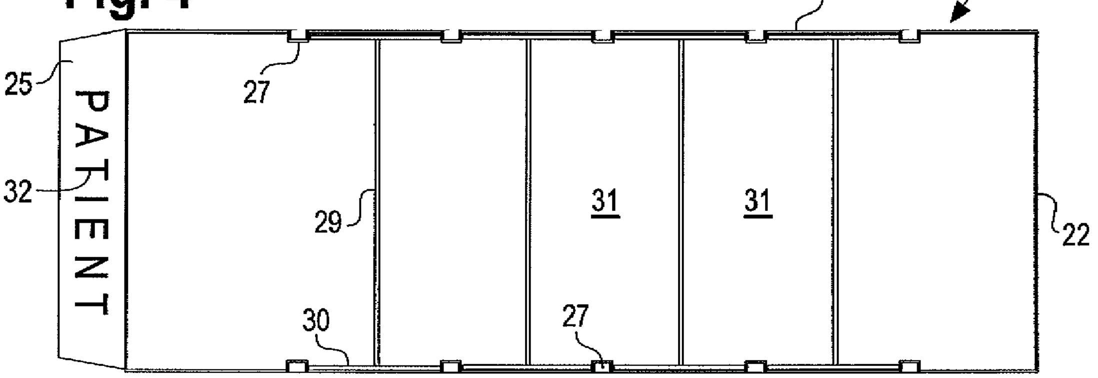
FIG. 4 is a top view of the drawer with inserted liner shown in FIG. 3.

The liner 20 may be made of any common and easily fabricated disposable material, such as injection- or vacuum-molded plastic. Preferably, liner 20 is made of bacteriostatic plastic. Dividers 28 are preferably made of the same material as the liner 20. Liners 20 and dividers 28 may be made in various colors or color combinations to allow for color coding according to patient or staff designations or any other desired classification system. The end tabs 30 may be sized to be complimentary to the ribs 27 and fit snugly between adjacent ribs 27 in the liner side panels 21 (see FIG. 4). When installed in the liner 20, the lower edge of the center panel 29 of the divider 28 is generally flush with the liner bottom 24. Dividers 28, as needed, may be inserted into the liner 20 to create smaller compartments 31 in the drawer 13. The identification tab 25 may be angled to overlay the identification plate 18 when the liner 20 is installed in the drawer 13. Patient information 32 is preferably affixed to the identification tab 25 to avoid the need to continually remove and replace patient information on the identification plate 18.

Figure 5:
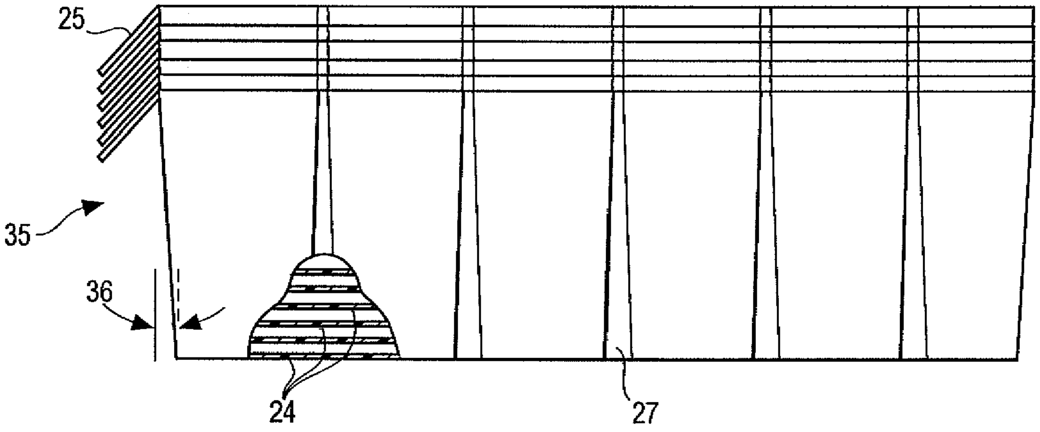
FIGS. 5 and 6 are side and perspective views, respectively, of a container holding nested stacks of drawer liners.

In an alternative embodiment, the tapered corners 26 of the liner 20 allow a plurality of liners 20 to be stored in a nested stack 35 (see FIG. 5). In the preferred embodiment, the taper angle 36 is such that the space between adjacent bottom panels 24 in a nested stack 35 is minimized. This sizing is for convenience in storage and retrieval of individual liners 20. When the liners 20 are tapered in this fashion, the dividers 28 are also tapered to fit within the liners.

Figure 6:
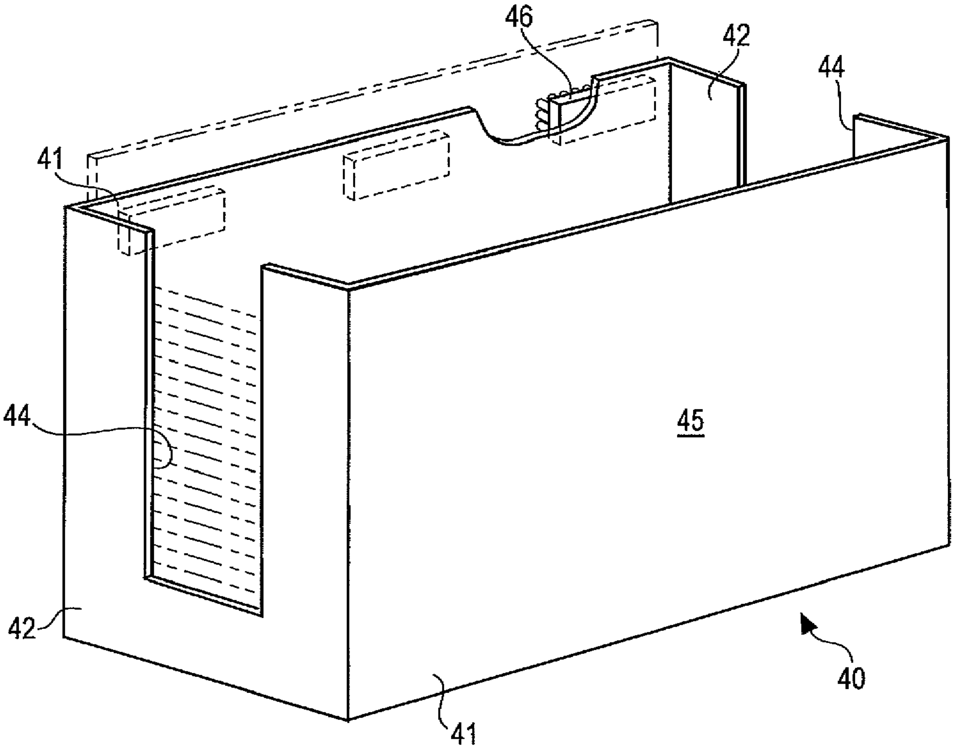

For the convenience of the user, the preferred embodiment includes a dispenser system 40 (see FIG. 6). The dispenser 40 is comprised of a rectangular container 45 with two side panels 41, two end panels 42, a bottom panel 43 and an open top. Alternatively, one or both end panels 42 may incorporate perforations to permit removal of a center portion to form openings 44. The container 45 is large enough to hold a nested stack 35 of liners. The end panels 42 may include a cut-out opening 44 wide enough for hand access to the liners 20 which are drawn out through the top. In a wall-mounted dispenser system, the dispenser 40 may also include mounting brackets 46 attached to a side panel 41 of the dispenser 40.

Dispensers 40 may be of a permanent or disposable type. A disposable dispenser 40 is preferably made of cardboard or similar material. A permanent dispenser 40 is preferably made of high impact plastic. In an alternative embodiment, a permanent dispenser 40 may be sized to hold a disposable dispenser 40. In either case, it is preferred that the dispenser 40 include a means to identify the color of the liners 20 being stored. Such means may include the use of color-coded labels, bar codes, windows and other techniques as are known in the art. In an alternative to the preferred embodiment, the drawer 13 need not be bottomless to obtain the benefits of the invention. While it is believed that the bottomless drawer 13 insures that a liner 20 is used and is therefore preferable, it is recognized that existing medication carts 10 have drawers 13 with bottoms 17 that are suitable for use with the invention. It is also recognized that medication carts 10 and drawers 13 have been and will be made in shapes other than regular geometric rectangles. It is within the scope of the invention then that liners 20, dividers 28, dispensers 40 and other components of the preferred embodiment may be of any shape that generally conforms to the interior contours of a drawer.

While the illustrated preferred embodiment is directed to use in medication carts 10, the principles of the invention are equally adaptable for other health care applications including other drug delivery systems, epidural trays, stock bins for unit dose (UD) dispensing, outpatient and home health care medicine receptacles, separation of narcotics, team-R carts, code carts, labor and delivery tackle boxes, cardiovascular operating room buckets, laboratory samples, intravenous solutions and other medical cabinets and storage systems as are known in the art.

Figure 7:
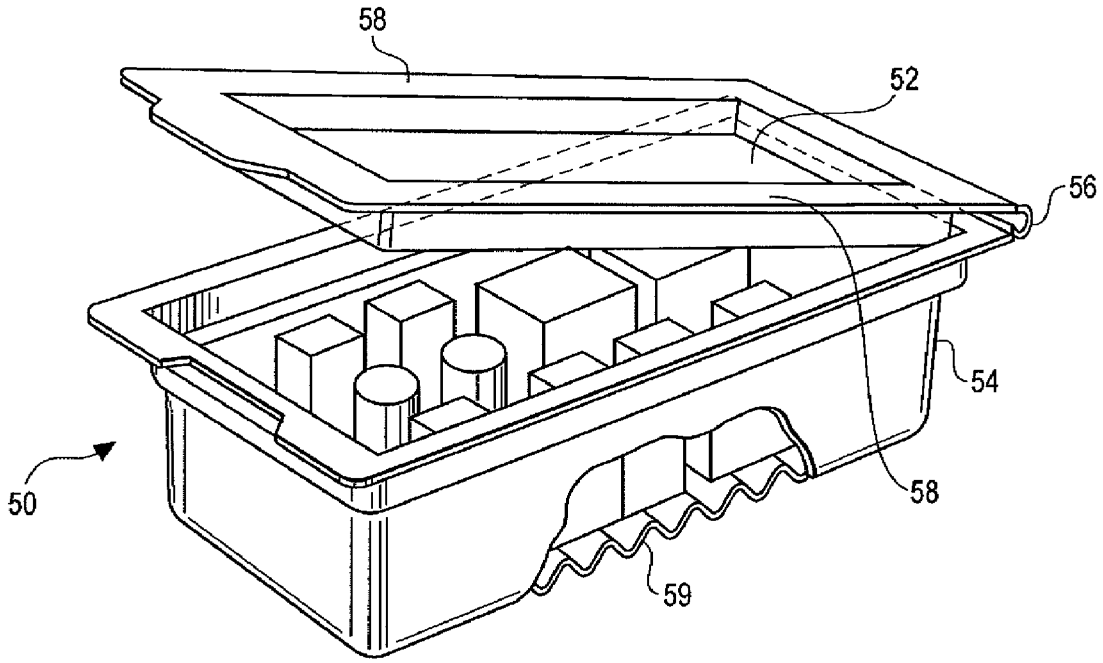
FIG. 7 is a perspective view of an alternative embodiment of a bin liner with a hingeable cover.

As illustrated in FIGS. 7-10, alternative forms of the bin liner may be designed to enhance its functionality. For example, the bin liner 50, illustrated in FIG. 7, is provided with a cover 52 which may be joined to the end wall 54 of the liner via a living hinge 56. Cover 52 may be opened and closed repeatedly and includes a peripheral flange 58 that effectively seals the contents within the bin when the liner cover is closed. The liner 50 and cover 52 may be easily fabricated using conventional plastic molding technology.

Figure 8:
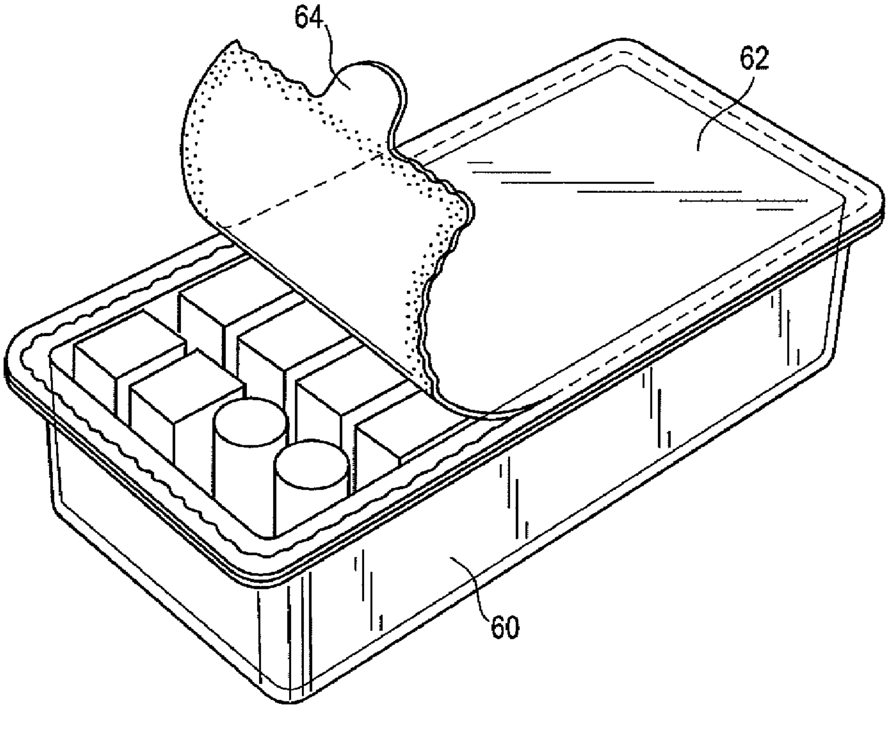
FIG. 8 is a perspective view of an alternative embodiment of a bin liner with a sealable, peelable cover.

Likewise, FIG. 8 illustrates a bin liner 60 having a peelable cover 62 which also seals the bin. A pull tab 64 may be employed to facilitate removal of the cover.

Figure 9:
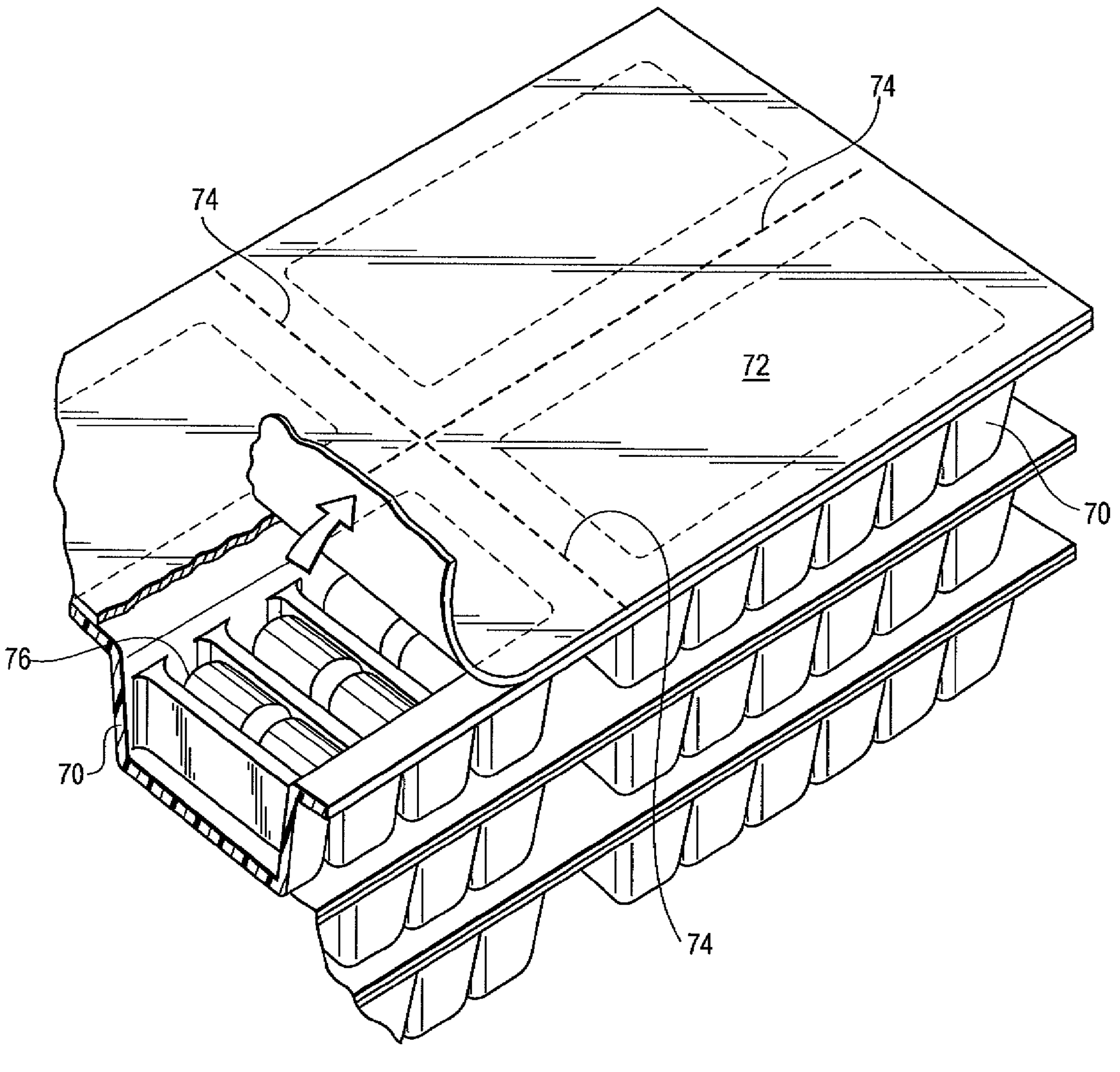
FIG. 9 is a perspective view of an array of bin liners with sealable, peelable covers.

FIG. 9 shows an array of bin liners 70, each having a cover 72. Each individual bin liner and its associated cover may be removed from the array simply by tearing along the perforated separation lines 74.

Figure 10:
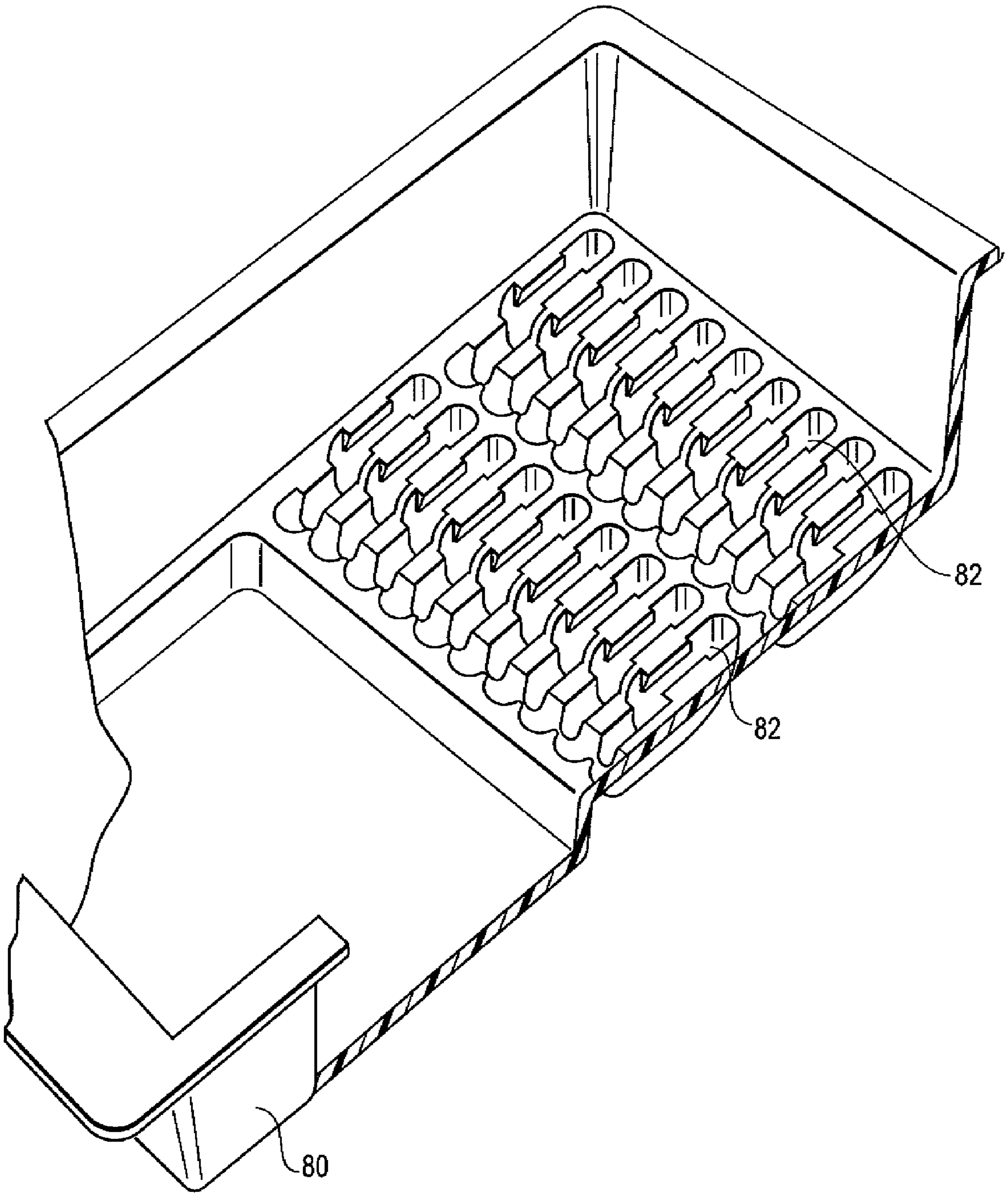
FIG. 10 is a partial perspective view of an alternative embodiment of a bin liner with ampule recesses.

The bin liners may also be provided with bottom walls having varying configurations. An "egg carton" arrangement is employed in the bin bottom 59, as shown in FIG. 7, to cushion the contents of the bin and thereby reduce the potential for breakage. Other arrangements, such as the package recesses 76 (as illustrated in FIG. 9) or the ampule recesses 82 used in bin liner 80 (as illustrated in FIG. 10) may also be advantageously employed.

Figure 11:
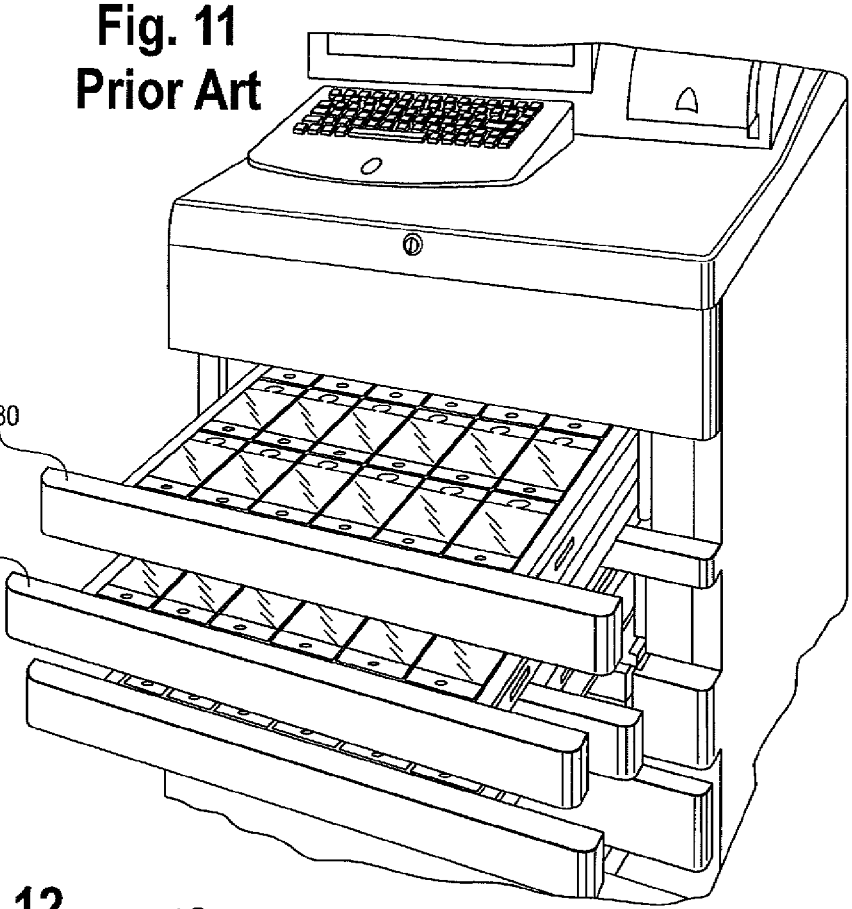
Fig. 11 Prior Art
FIG. 11 is a partial perspective view of a prior art medication dispensing machine, showing some of the drawers already opened.
Figure 12:
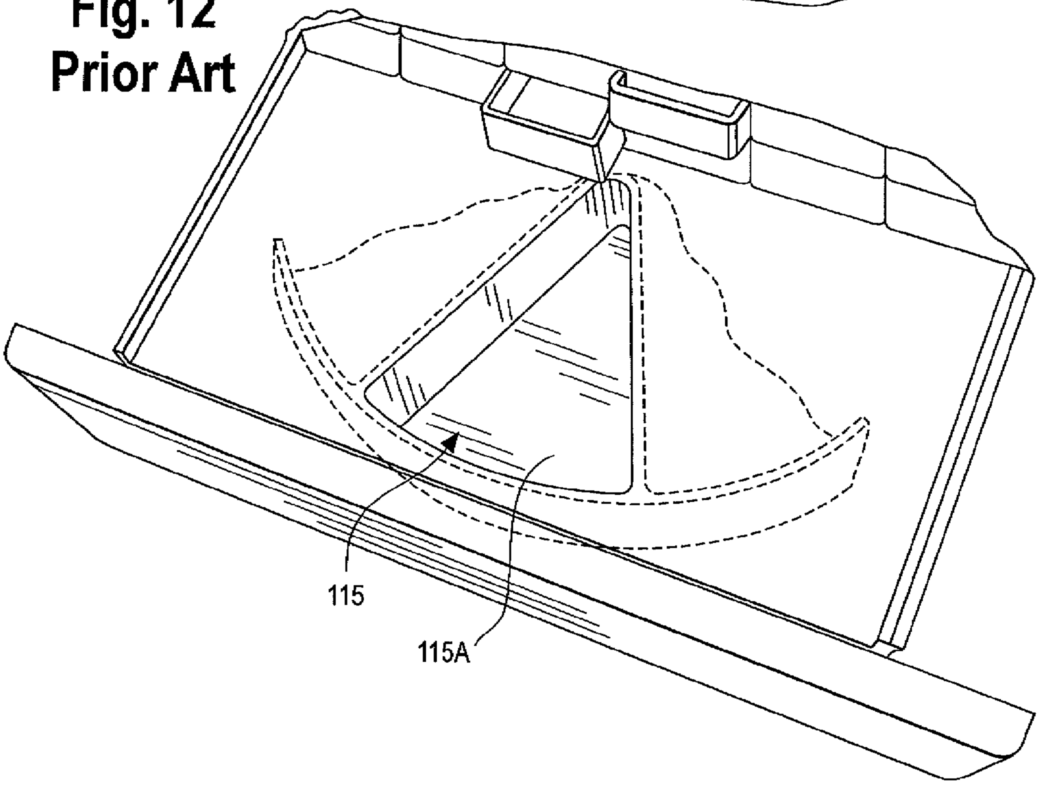
Fig. 12 Prior Art
FIG. 12 is a partial perspective view of a drawer with a pie-shaped compartment for storing medication.

Referring now to FIG. 11, an automatic dispensing machine (ADM) 100 of a type well known in the art is shown. Such ADMs are known by their manufacturing names, such as "Pyxis" and "Omnicell" machines. These ADMs include a computer programmed to enable medical personnel to key in a password or other identifier information, to reveal a screen showing individual patient information. When appropriate information is transmitted to the computer, an individual drawer 110 may be automatically opened, enabling medical personnel to access the individual medication bins within the desired drawer. Drawers 110 may include various compartments ("matrix drawers") which may be lined with (typically plastic) drawer liners 115 (see FIGS. 12, 14 and 15A-15C) forming individual compartments or "pockets" 115A which may have various sizes and shapes, depending upon the type of medication to be stored there. Drawers 110 may also include "cubies" or other specialty compartments as further explained below. Drawers 110 useful with the present invention may also have bottoms, or may be bottomless.

Figure 13B:
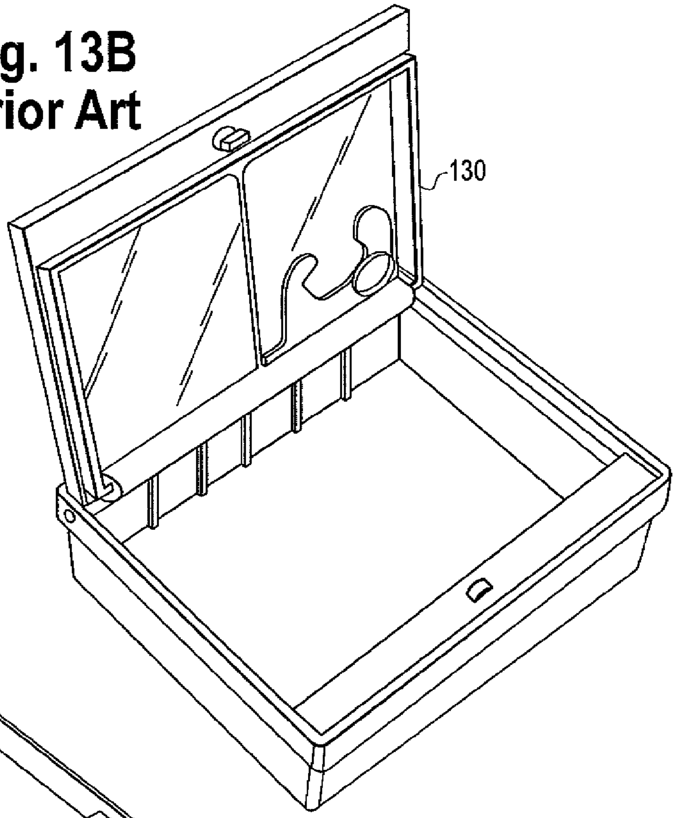
Fig. 13B Prior Art
FIGS. 13A-13C are perspective views of various prior art individual bin which may be placed in the drawers shown in FIG. 11.
Figure 13A:
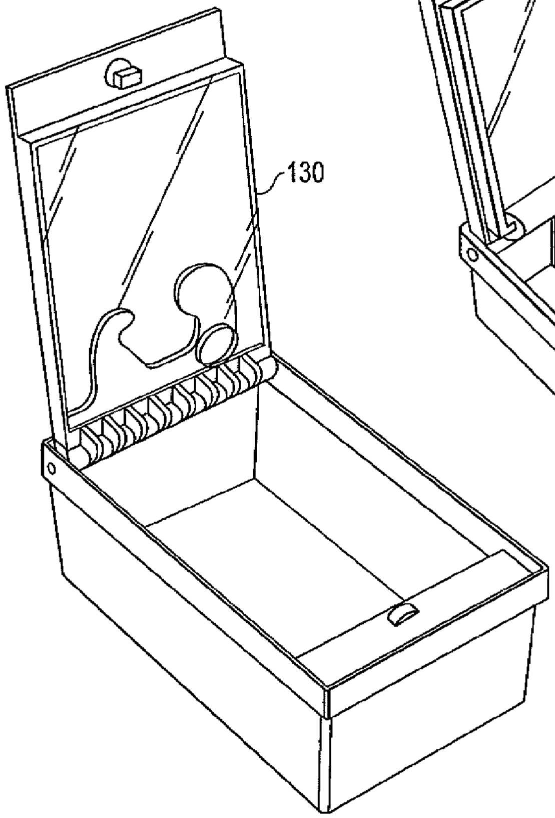
Fig. 13A Prior Art
Figure 13C:
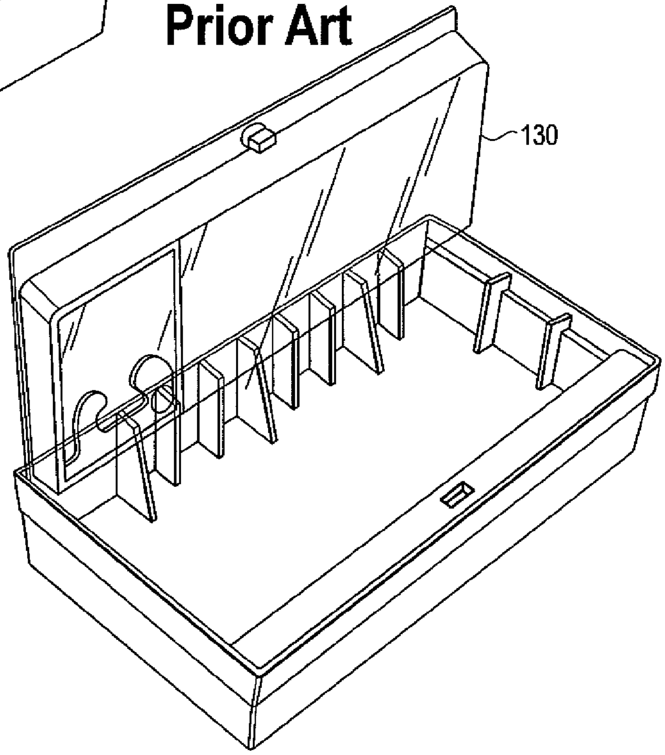
Fig. 13C Prior Art
Figure 19:
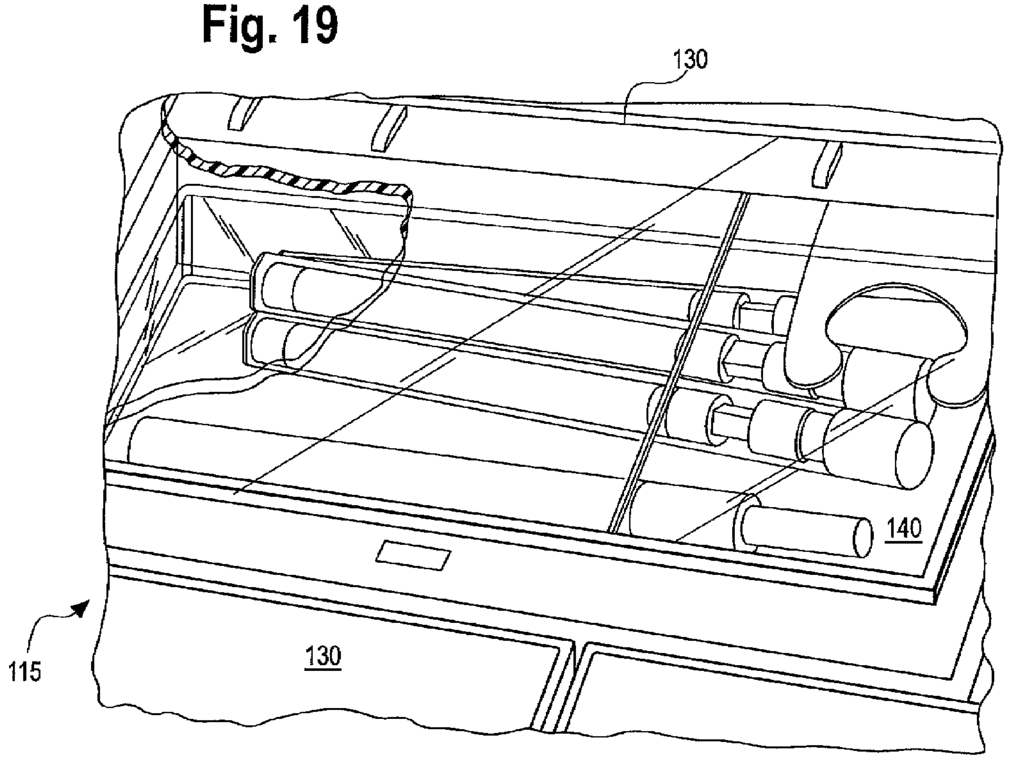
FIG. 19 is a perspective view of a drawer liner compartment, and inserted bin liner.
Figure 20:
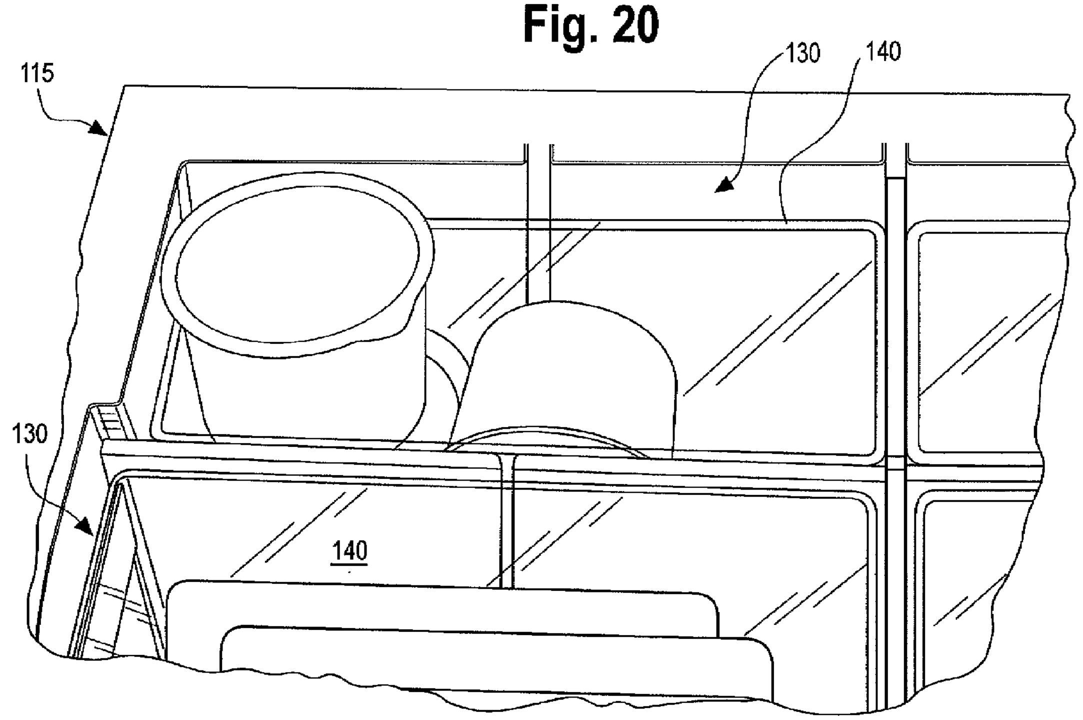
FIG. 20 is a perspective view of an alternative drawer liner compartment, and inserted bin liner.

Referring to FIGS. 13A-13C, certain drawers 100 may include individual integral compartments known as "cubies" 130, which may have hingeable covers 130A or not. Cubies 130 have an electronic interface (not shown) for direct connection to a socket located on an interior surface of the ADM drawer. When medical personnel select a cubic within a particular drawer, both the selected drawer and the selected cubie automatically open, while the other cubies within the open drawer remain closed, for both security and inventory control purposes. According to the present invention, each cubie 130 may be outfitted with an insertable plastic, disposable drawer liner bin 115A, as well. Referring to FIGS. 19 and 20, there are also "mini" drawers 150 which are similar to cubies, except that they have different shapes, such as an elongated rectangular shape, and are typically used for narcotics or other expensive medications (to maintain inventory control). "Minis," like cubies, are electronically connected and only may be opened if the proper information is supplied to the ADM computer, and then only the designated mini within a drawer will open, not other minis or cubies within that drawer. As with cubies, minis may be provided with disposable plastic liners 140.

To summarize, cubie and mini compartments allow limited access, while matrix compartments do not. The matrix drawer is used for drugs not requiring a high level of security and/or inventory control.

Figure 16:
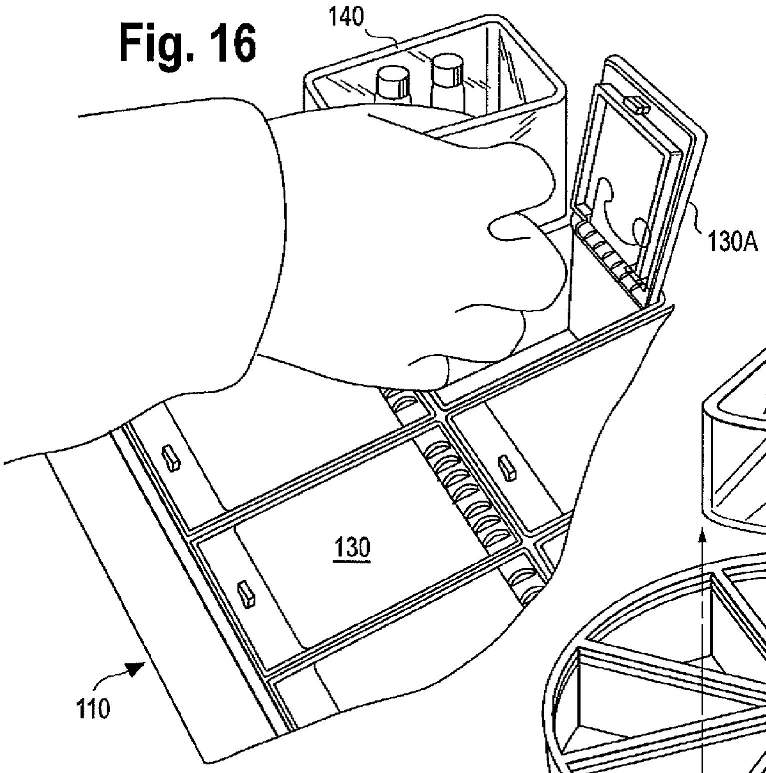
FIGS. 16-18 are perspective views of various plastic bin liners having different geometric configurations shaped to correspond with that of the bins of the drawer liners.
Figure 17:
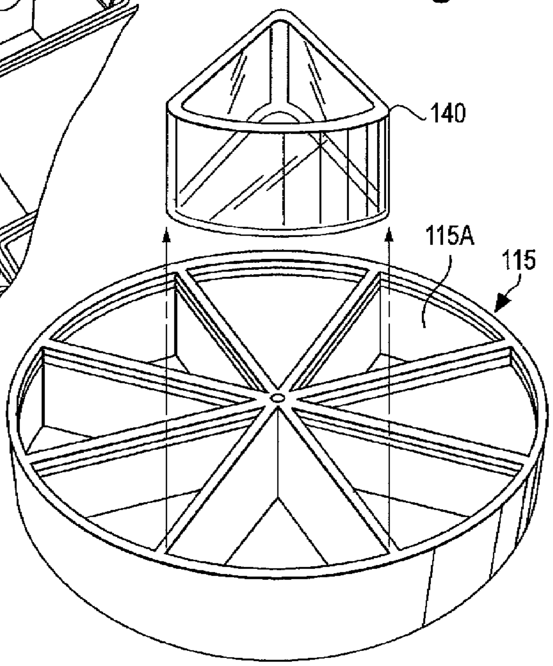
Figure 18:
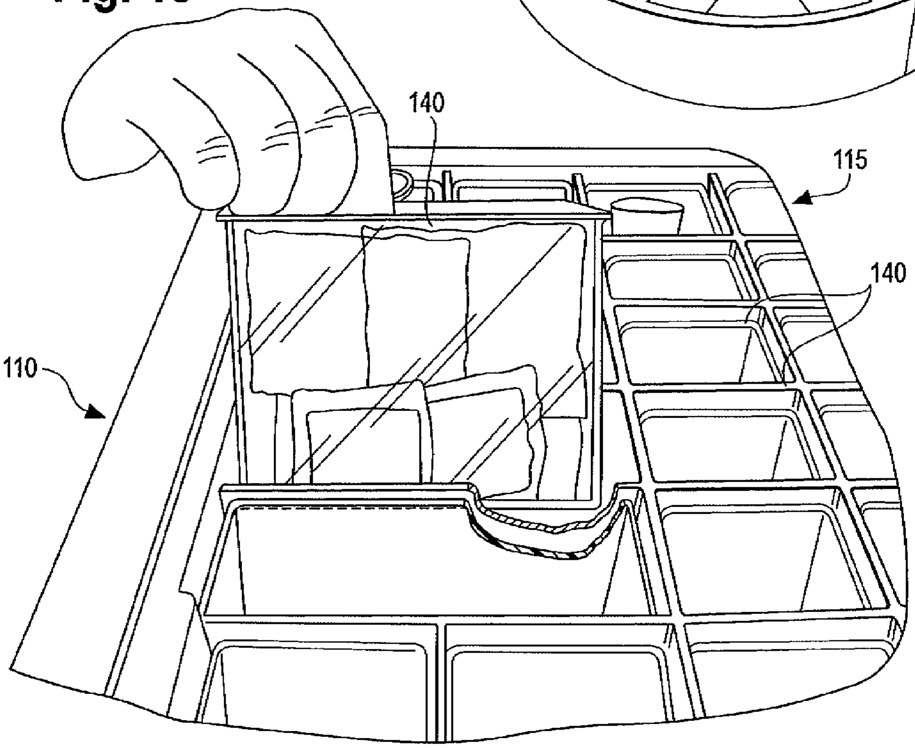
Figure 17A:
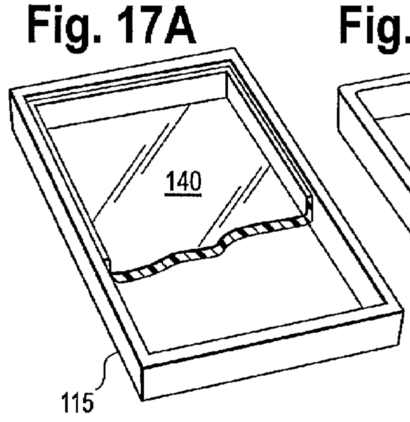
FIGS. 17A-17F and 18A-18C are perspective views of various bin shapes of drawer liners housing inserted bin liners with corresponding shapes.
Figure 17B:
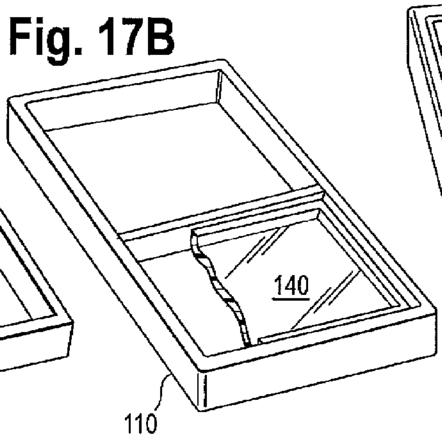
Figure 18A:
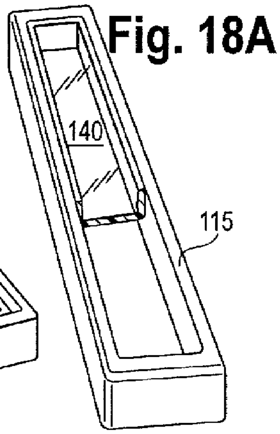
Figure 17C:
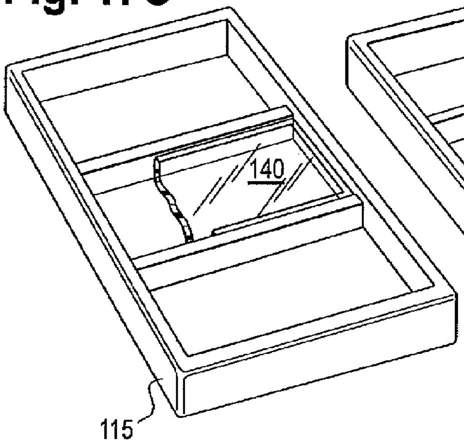
Figure 17D:
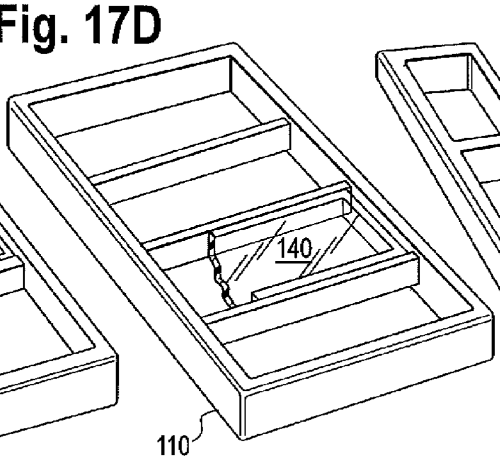
Figure 18B:
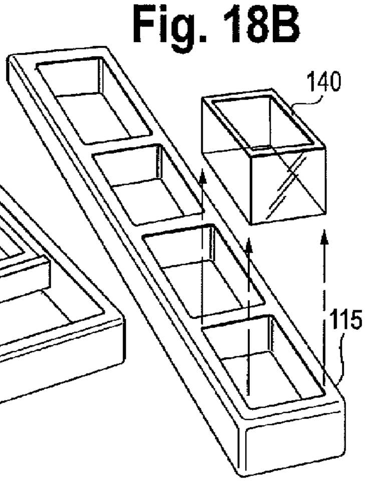
Figure 17E:
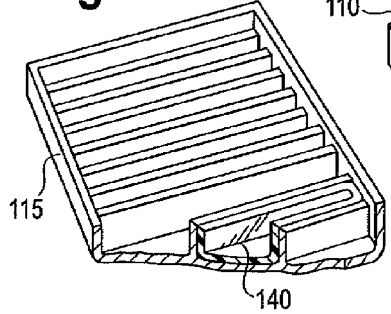
Figure 17F:
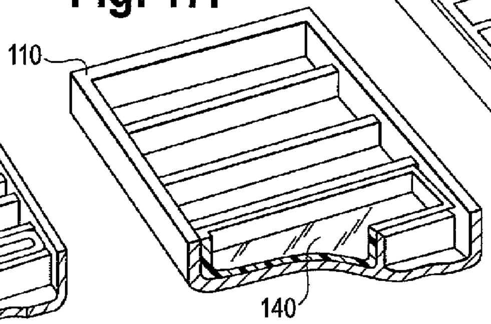
Figure 18C:
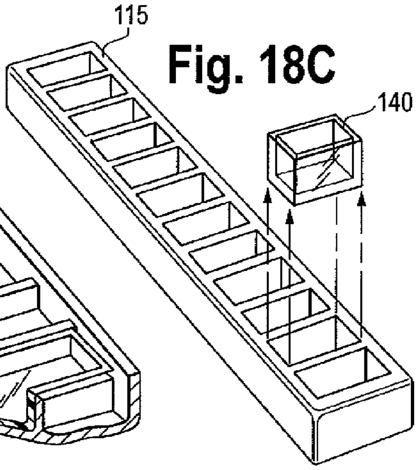

As should now be understood given the above description, the use of drawer liners 115 has been discovered by the inventor to be a particular source of the spread of nosocomial infections due to cross-contamination and ineffective cleaning. Simply put, medical personnel fail to clean drawer liners on any kind of consistent or periodic basis, and also do not clean them anywhere close to often enough. Given the inventor's surprising discovery in this regard, his solution largely solved the problem: individual, disposable plastic bin liners 140 (see, e.g., FIGS. 16-18), which may be inserted into the bins formed by drawers 110 or drawer liners 115. The individual bins are much easier to clean: only the contents of the single compartment liner 140 need be removed, and the liner may then be discarded and replaced with another. (In contrast, without the use of plastic, disposable bin liners, the entire contents of the drawer and/or drawer liner must be removed in order for the drawer and/or drawer liner to be cleaned. This often resulted in destruction of various medications in such contaminated drawers/liners.) Further, drawers and/or drawer liners may be difficult to clean given gummy label residue, and the residue of various, spilled medications. The use of individual, disposable compartment liners removes this problem.

Compartment liners may be made in any size and configuration, to fit the size of individual drawer compartments and/or drawer liner compartments, as shown in FIGS. 17A-17F and 18A-18C. Referring to FIGS. 19 and 20, "mini" compartments 130 may be outfitted with disposable plastic compartment liners 140 to carry medication or drugs which carry security risks, require a careful degree of inventory control and/or are odd-shaped (e.g., glass cartridges, ampoules, peelable containers).

With matrix drawers, it is preferred that drawer liners be used, as their use can preserve the integrity of the bins themselves (i.e., when drawers without drawer liners are used, spilled liquid medications containing dextrose, fatty acids or other substances can leak from pocket to pocket and quickly grow microorganisms, for example). Individual plastic, disposable bin liners therefore find particularly advantageous use with ADMs or manual medication carts in which matrix drawers with individual compartments, but without drawer liners, are used. However, for cleaning efficiency (and to avoid drug destruction during wholesale cleaning of drawers without compartment liners), even when drawer liners are used, individual, disposable bin liners of the present invention find great advantage, as well, for the reasons discussed above.

In another aspect of the invention, drawer liners 115, or individual bin liners 140, may be color-coded to differentiate the presence of certain medications. As non-limiting examples: blue drawer liners and/or blue bin liners may be used to signal the presence of innocuous or common drugs (e.g., Tylenol®, aspirin); green could be used to signal the presence of "look-a-like" drugs (e.g., those with a similar physical appearance, such as those consisting of round white tablets, or drugs with sound-a-like names such as diphenhydramine and dimenhydrinate); and red could be used to signal the presence of potentially dangerous drugs if administered improperly (e.g., antibiotics similar to penicillin, due to potential allergic reactions; drugs with a narrow therapeutic window, such as digoxin, in which slightly more than recommended could result in toxic levels, drugs with very pronounced therapeutic effects such as "pressors" that increase blood pressure or those taken for sepsis/blood infection, and highly addictive drugs such as morphine).

The above description is not intended to limit the meaning of the words used in the following claims that define the invention. Rather, it is contemplated that future modifications in structure, function or result will exist that are not substantial changes and that all such insubstantial changes in what is claimed are intended to be covered by the claims.

We claim:

1. A medication storage apparatus minimizing the threat of nosocomial infection caused by cross-contamination of fomites, comprising:

one or more drawers designed for reception into the apparatus, the drawer having adjoining walls defining at least one enclosed space;

at least one primary liner supported by and sized to fit within a drawer, the primary liner having a plurality of dividers defining a plurality of compartments which can either be uniformly or disparately sized;

a plurality of secondary liners, each sized and shaped to hold medications, supplies or equipment and to be removably inserted into one of the correspondingly-sized compartments of the primary liner such that each said inserted second liner occupied substantially the entire correspondingly-sized compartment, the secondary liners being disposable to minimize cross-contamination;

wherein the medication storage apparatus minimizes the threat of nosocomial infection by enabling an apparatus user to periodically dispose of the secondary liners and to replace them with new, sanitary liners.

2. The medication storage apparatus of claim 1, wherein the medication storage apparatus comprises an automatic dispensing machine in which compartments of the primary liner are designed to electronically interconnect with the drawer.

3. The medication storage apparatus of claim 1, wherein the secondary liners comprise a thin, plastic material which is either clear or opaque.

4. The medication storage apparatus of claim 1, wherein the secondary liners comprise a bacteriostatic plastic.

5. The medication storage apparatus of claim 1, wherein at least two or more of the plurality of secondary liners are color-coded within a color-coding scheme including two or more color designations, with each different color designation indicating the type or class of medications, supplies or equipment contained within the color-coded liner or to a patient-specific risk or condition.

6. The medication storage apparatus of claim 5, wherein two or more color designations within the color-coding scheme are used to indicate the presence of medications having one or more of the following attributes: addicting; a similar-sounding name; look-alikes; innocuous or common in attributes or use; low therapeutic window; or pronounced therapeutic effects.

7. The medication storage apparatus of claim 1, wherein at least one of the at least one primary liner and the plurality of secondary liners contains individual, patient-specific information.

8. The medication storage apparatus of claim 1, wherein the apparatus includes a plurality of drawers, and two or more of the drawers each include a primary liner.

9. The medication storage apparatus of claim 1, wherein the drawer comprises a bottomless drawer.

10. A method for reducing nosocomial infection in a hospital or other medical patient care facility caused by cross-contamination of fomites, comprising the steps of:

providing a medication storage apparatus having one or more drawers designed for reception within the apparatus, the drawers each having adjoining walls defining at least one enclosed space;

positioning at least one primary liner so that it is supported by and fits within a drawer, the primary liner having a plurality of dividers defining a plurality of compartments which may either be uniformly or disparately sized;

positioning a plurality of second liners within correspondingly-sized compartments of the at least one primary liner, the secondary liners each sized and shaped to hold medications, supplies or equipment and to be removably inserted into one of the compartments of the at least one primary liner, such that each said inserted second liner occupied substantially the entire correspondingly-sized compartment;

placing medications, supplies or equipment within the plurality of secondary liners;

transporting the medication storage apparatus to an area adjacent users of the medications, supplies or equipment, and providing the users with or using them in connection with, the medications, supplies or equipment;

periodically removing at least the plurality of secondary liners from the compartments and disposing of the secondary liners; and positioning new secondary liners within their corresponding compartments.

11. The method of claim 10, wherein the area adjacent users of the medications, supplies or equipment comprises a hospital room or hospital hallway.

12. The method of claim 10, further comprising the step of periodically removing the at least one primary liner from its corresponding drawer to clean the at least one primary liner.

* * * * *